US008757164B2

(12) United States Patent
Abramson

(10) Patent No.: US 8,757,164 B2
(45) Date of Patent: *Jun. 24, 2014

(54) DENTAL APPLIANCE WITH ADJUSTABLE TONGUE REPOSITIONER

(76) Inventor: Mark E. Abramson, Redwood City, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 13/589,728

(22) Filed: Aug. 20, 2012

(65) Prior Publication Data

US 2013/0037037 A1     Feb. 14, 2013

Related U.S. Application Data

(63) Continuation of application No. 12/854,343, filed on Aug. 11, 2010, now Pat. No. 8,256,426.

(60) Provisional application No. 61/233,250, filed on Aug. 12, 2009.

(51) Int. Cl.
*A61F 5/56* (2006.01)
*A61C 5/14* (2006.01)

(52) U.S. Cl.
USPC .......................................... 128/848; 128/861

(58) Field of Classification Search
USPC .......... 128/848, 859–862; 433/6–7, 136, 138, 433/148–149, 160; 602/902
See application file for complete search history.

(56) References Cited

U.S. PATENT DOCUMENTS

| 1,674,336 | A | 6/1928 | King |
| 2,685,287 | A | 1/1953 | Golfier et al. |
| 2,705,006 | A | 3/1955 | Cettel |
| 3,943,924 | A | 3/1976 | Kallestad et al. |
| 4,044,762 | A | 8/1977 | Jacobs |
| 4,063,552 | A | 12/1977 | Going et al. |
| 4,114,614 | A | 9/1978 | Kesling |
| 4,337,765 | A | 7/1982 | Zimmerman |
| 4,419,992 | A | 12/1983 | Chorbajian |
| 4,457,708 | A | 7/1984 | Dufour |
| 4,462,800 | A | 7/1984 | Jones |
| 4,471,771 | A | 9/1984 | Steven et al. |
| 4,669,459 | A | 6/1987 | Sprewek et al. |

(Continued)

FOREIGN PATENT DOCUMENTS

| EP | 0801937 | 10/1997 |
| GB | 2264868 | 9/1993 |
| WO | 9851234 | 11/1998 |

OTHER PUBLICATIONS

International Searching Authority, "International Search Report and Written Opinion for PCT/US2010/045366", dated Oct. 20, 2010, 11 pages.

*Primary Examiner* — Patricia Bianco
*Assistant Examiner* — Ophelia A Hawthorne
(74) *Attorney, Agent, or Firm* — Meyer IP Law Group

(57) ABSTRACT

An embodiment of a device in accordance with the present invention is adapted to be positioned at least partially in a mouth of a user to reduce resistance of air flow in the oral pharyngeal region and to improve anatomic and functional relationships of the oral pharyngeal structure. The device comprises a base unit adapted to be removably mounted on a lower jaw of the mouth, a pair of tongue positioner guides, each tongue positioner guide connected at a proximal end to the base unit, and a pair of tongue positioners, each connected with a distal end of a corresponding tongue positioner guide. The tongue positioner guides each comprise a bendable material so that the pair of tongue positioners are repositionable relative to the base unit.

20 Claims, 16 Drawing Sheets

(56) References Cited

U.S. PATENT DOCUMENTS

| | | |
|---|---|---|
| 4,715,368 A | 12/1987 | George |
| 4,901,737 A | 2/1990 | Toone |
| 5,003,994 A | 4/1991 | Cook |
| 5,038,047 A | 8/1991 | Still |
| 5,055,039 A | 10/1991 | Abbatte et al. |
| 5,056,534 A | 10/1991 | Wright |
| 5,059,118 A | 10/1991 | Breads et al. |
| 5,063,940 A | 11/1991 | Adell et al. |
| 5,066,226 A | 11/1991 | Summer |
| 5,067,896 A | 11/1991 | Korn |
| 5,082,007 A | 1/1992 | Adell |
| 5,092,346 A | 3/1992 | Hayes et al. |
| 5,103,838 A | 4/1992 | Yousif |
| 5,117,816 A | 6/1992 | Shapiro et al. |
| 5,152,301 A | 10/1992 | Kittelsen et al. |
| 5,163,840 A | 11/1992 | Bourke |
| 5,165,424 A | 11/1992 | Silverman |
| 5,174,284 A | 12/1992 | Jackson |
| 5,176,514 A | 1/1993 | Viazis |
| 5,186,623 A | 2/1993 | Breads et al. |
| 5,203,351 A | 4/1993 | Adell |
| 5,234,005 A | 8/1993 | Kittelsen et al. |
| 5,235,991 A | 8/1993 | Minneman |
| 5,259,762 A | 11/1993 | Farrell |
| 5,293,880 A | 3/1994 | Levitt |
| 5,316,020 A | 5/1994 | Truffer |
| 5,265,945 A | 11/1994 | Holstrom |
| 5,365,945 A | 11/1994 | Halstrom |
| 5,409,017 A | 4/1995 | Lowe |
| 5,499,633 A | 3/1996 | Fenton |
| 5,566,683 A | 10/1996 | Thornton |
| 5,570,704 A | 11/1996 | Buzzard et al. |
| 5,665,104 A | 9/1997 | Lee |
| 5,727,543 A | 3/1998 | Corsaro |
| 5,752,822 A | 5/1998 | Robson |
| 5,755,219 A | 5/1998 | Thornton |
| 5,794,627 A | 8/1998 | Frantz et al. |
| 5,823,193 A | 10/1998 | Singer et al. |
| 5,884,628 A | 3/1999 | Hilsen |
| 5,921,241 A | 7/1999 | Belfer |
| 5,922,006 A | 7/1999 | Sugerman |
| 6,109,265 A | 8/2000 | Frantz et al. |
| 6,170,485 B1 | 1/2001 | Orrico |
| 6,325,064 B1 | 12/2001 | Thornton |
| 6,328,754 B1 | 12/2001 | Marten et al. |
| 6,375,667 B1 | 4/2002 | Ruch |
| 6,390,089 B1 | 5/2002 | Lacouture |
| 6,405,729 B1 | 6/2002 | Thornton |
| 6,446,631 B1 | 9/2002 | Hagiwara |
| 6,450,167 B1 | 9/2002 | David et al. |
| 6,478,023 B1 | 11/2002 | Lockwood |
| 6,516,805 B1 | 2/2003 | Thornton |
| 6,766,802 B1 | 7/2004 | Keropian |
| 6,769,910 B1 | 8/2004 | Pantino |
| 6,802,079 B2 | 10/2004 | Bush |
| 6,805,127 B1 | 10/2004 | Karasic |
| 6,820,617 B2 | 11/2004 | Robertson et al. |
| 6,820,623 B2 | 11/2004 | Cook |
| 6,837,246 B1 | 1/2005 | DeLuke |
| 6,851,424 B2 | 2/2005 | Scopton |
| 6,886,567 B1 | 5/2005 | Liu |
| 6,932,087 B1 | 8/2005 | Burns |
| 6,932,088 B1 | 8/2005 | Berghash |
| 6,935,857 B1 | 8/2005 | Farrell |
| 6,941,952 B1 | 9/2005 | Rush |
| 6,951,678 B2 | 10/2005 | Takeshita et al. |
| 6,986,354 B1 | 1/2006 | Burns |
| 7,077,646 B2 | 7/2006 | Hilliard |
| 7,128,072 B2 | 10/2006 | Bancroft |
| 7,175,427 B2 | 2/2007 | Smith |
| 7,178,520 B2 | 2/2007 | Scopton |
| 7,178,529 B2 | 2/2007 | Kownacki |
| 7,182,086 B2 | 2/2007 | Fujieda et al. |
| 7,210,483 B1 | 5/2007 | Lesniak et |
| 7,255,108 B2 | 8/2007 | Loughlin |
| 7,299,804 B2 | 11/2007 | Kittelsen et al. |
| 7,328,705 B2 | 2/2008 | Abramson |
| 7,328,706 B2 | 2/2008 | Bardach et al. |
| 7,353,828 B1 | 4/2008 | Hirshberg |
| 7,404,403 B2 | 7/2008 | Farrell |
| 7,404,404 B2 | 7/2008 | Lombardi |
| 7,422,017 B2 | 9/2008 | Bancroft |
| 7,451,767 B2 | 11/2008 | Keropian |
| 7,481,773 B1 | 1/2009 | Dorroh et al. |
| 7,506,651 B2 | 3/2009 | Anonsen |
| 7,530,355 B2 | 5/2009 | Berghash |
| 7,549,423 B1 | 6/2009 | Hirshberg |
| 7,581,542 B2 | 9/2009 | Abramson |
| 2004/0013993 A1 | 1/2004 | Ito |
| 2006/0112962 A1 | 6/2006 | Tebbutt et al. |
| 2006/0289013 A1 | 12/2006 | Keropian |
| 2008/0210244 A1 | 9/2008 | Keropian |
| 2009/0056724 A1 | 3/2009 | Keropian |
| 2009/0120448 A1 | 5/2009 | Keropian |

DENTAL APPLIANCE WITH ADJUSTABLE TONGUE REPOSITIONER

CLAIM OF PRIORITY

This application is a Continuation of U.S. patent application Ser. No. 12/854,343, entitled "MODULAR DENTAL APPLIANCE FOR IMPROVING AIRFLOW THROUGH NASAL-PHARYNGEAL AIRWAYS," filed Aug. 11, 2010, which is now U.S. Pat. No. 8,256,426, and which claims the benefit of U.S. Provisional Application No. 61/233,250, filed Aug. 12, 2009, both of which are hereby incorporated by reference herein.

FIELD OF THE INVENTION

This invention relates to appliances for affecting air flow through the nasal and posterior pharyngeal regions of the upper airway.

BACKGROUND

Upper airway resistance to airflow afflicts millions of individuals and can have very serious medical consequences including significant morbidity and mortality. The health effects are brought about by the disruption of normal sleep with snoring and sleep apnea (i.e. a complete stoppage of breathing for a period of time). The effects of snoring and sleep apnea may also compromise the well being of those sleeping in proximity to the afflicted person by disrupting their ability to achieve healthy, restful sleep.

Sleep is impacted by both the increased effort needed to overcome increased resistance to airflow and by the fragmentation of sleep patterns brought about by awakenings that occur in both hyponia (i.e. reduced air flow) and apneic events (i.e. periods of stoppage of air flow). These conditions limit one's ability to enter deeper stages of sleep that are necessary to refresh and restore and are damaging to many body systems.

The primary treatment for snoring and apnea is the use of a device, referred to as a continuous positive air pressure (CPAP) device. The CPAP device delivers pressurized air from a pumping component through a hose to a mask which is secured over the nose of the individual. The CPAP device can be successful at correcting the problem but it is not well tolerated by a significant group of individuals due to discomfort and lifestyle issues, and due to the lack of portability of the CPAP device. Because of these factors a significant number of patients are forced to abandon the use of this therapy.

Surgical techniques that attempt to permanently correct snoring problems encountered by individuals have been available for many years. However, surgical techniques are complicated and invasive and sometimes permanently change the appearance of the individual. In addition, numerous medical drawbacks are inherent in surgical procedures, including cost, irreversibility, surgical risk, and long painful recovery periods.

Numerous alternative devices have been developed which attempt to alleviate or eliminate snoring problems without invasive surgery. Some devices have focused on improving airflow through the nose. These devices are used both in awake periods, during increased demand such as athletic usage, and during sleep to improve airflow as an anti-snoring device. One such device, taught in U.S. Pat. No. 6,375,667 to Ruch, attaches to the external skin along the right and left sides of the nose by means of adhesives. The device is spring biased and pulls the skin outward to strengthen and expand the nasal passages. However, the device of Ruh '667 is disposable and the adhesives can irritate the skin. Another device, taught in U.S. Pat. No. 5,727,543 to Corsaro, is designed to fit inside the nasal airway and push the inner walls of the nose out, expanding the air passage. The device of Corsaro '543 can irritate the sensitive inner lining of the mucosa of the nasal airway and is awkward to use.

Other devices have been developed which attempt to alleviate or eliminate snoring problems without invasive surgery by repositioning the lower jaw (mandible) in an anterior (forward) direction. The repositioning pulls the base of the tongue forward, thereby increasing the air passage in the posterior pharyngeal region (i.e. the breathing passage behind the base of the tongue). Devices which bring the mandible forward into a functional repositioning posture, and which hold the posterior airway open can be adjustable or non-adjustable. A non-adjustable device fits in the mouth at a prescribed position. The disadvantage of this is that there are changes that occur over time which require the position of the mandible in relationship to the maxilla to be changed. Available adjustable devices arrange significant components inside the mouth behind the teeth. These components take up space inside the mouth, restricting the space for the tongue and preventing the tongue from coming forward. Some devices also have projections which extend from the mouth out between the lips. These affect the user's ability to close their lips, making the appliance less comfortable and inhibiting the ability of the user to turn to different positions during sleep.

Simpler devices have recently been developed to treat sleep apnea. One such device is THE FULL BREATH SOLUTION®, developed by the Full Breath Corporation of Tarzana, Calif., which prevents blockage of the throat by the tongue by holding the base of the tongue down and forward. However, such devices rely on materials positioned at the back of the throat which can cause gagging.

There is a need for devices and techniques to improve airflow in nasal-pharyngeal airways that reduce or eliminate the disadvantages of available treatments.

| | | | |
|---|---|---|---|
| 102/202/ 402/402 | base unit | 104 | lingual wall |
| 106 | lateral wall | 108 | occlusal wall |
| 110/210 | ratchet housing | 111/211 | pawl |
| 114 | modular attachment point | 118 | bite surface |
| 120 | nasio-labial dilator | 122 | dilator stem |
| 130 | maxillary repositioning flange | 131 | dilator stem pocket |
| 132 | support shelf | 133 | support shelf pocket |
| 134 | access port | 135 | stem connection point |
| 136/236 | ratchet | 137/237 | ratchet teeth |
| 139 | support stem pocket | 140/340 | pos. vestibular pad support |
| 142 | brace | 144 | tines |
| 146/346 | posterior vestibular pad | 150 | anterior vestibular pad support |
| 152 | pad stem | 153 | upper injection port |
| 154 | anterior pad valve | 155 | lower injection port |
| 156 | anterior vestibular pad | 158 | flange spacing pad |
| 159 | support stem | 160 | tongue positioner guide |
| 162 | tongue positioner | 403 | occlusal chamber |
| 430 | maxillary flange | 456 | anterior vestibular pad |

DETAILED DESCRIPTION

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

Figure 1:
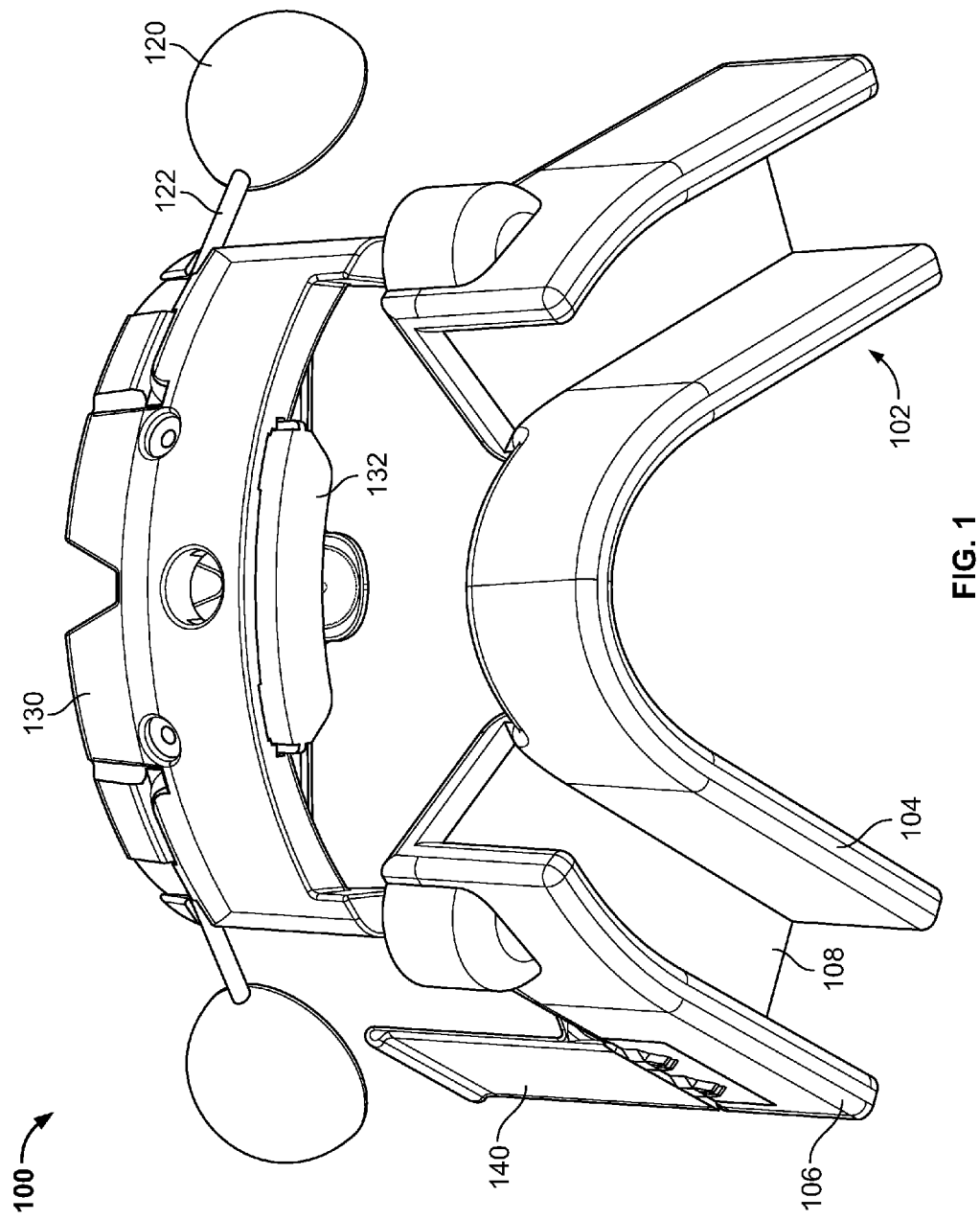
FIG. 1 is an anterior view of an embodiment of a modular device in accordance with the present invention adapted to dilate the nasal airways and reduce resistance of air flow in the pharyngeal region.
Figure 2:
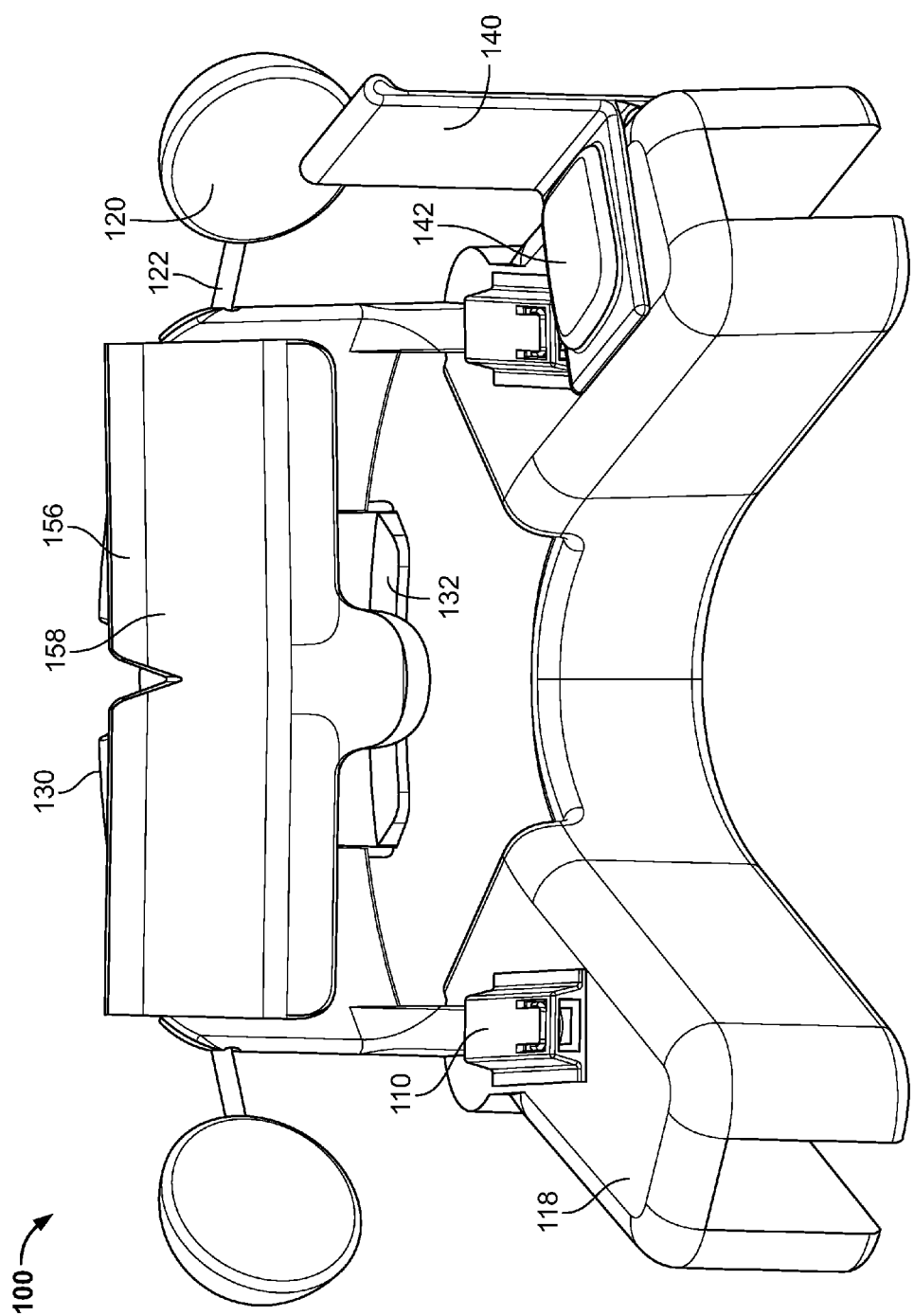
FIG. 2 is a posterior view of the modular device of FIG. 1.

FIG. 1 is an anterior perspective view and FIG. 2 is a posterior perspective view of an embodiment of a modular device 100 in accordance with the present invention for dilating the nasal airways and/or for improving anatomic and functional relationships of the oral pharyngeal structure of a patient, thereby reducing and/or eliminating at least some undesired effects of sleep apnea such as snoring. The modular device 100 comprises a base unit 102 including a lingual wall 104 and a lateral wall 106 connected by an occlusal wall 108. The base unit 102 is mounted on the mandible by seating the teeth of the mandible within a pocket formed between the lingual wall 104 and the lateral wall 106. As shown, the lingual wall 104 spans from the left molar to the right molar uninterrupted and the lateral wall 106 is gapped along at least the central incisors of the mandible. However, in other embodiments one or both of the lingual wall 104 and lateral wall 106 can be interrupted and/or uninterrupted. In still other embodiments, one or both of the lingual wall 104 and lateral wall 106 can be partially interrupted. For example, the lateral wall 106 can extend partially over the respective teeth. The walls of the base unit 102 need only be shaped to satisfactorily secure the base unit 102 to the lower dental arch so that the modular device 100 is held within the mouth of the patient without slippage or undesired movement.

The base unit 102 can be made of any material which can be used to secure the lower dental arch, such as processed acrylics, hard-molded outer shell material with a soft inner lining, boil-and-bite materials, pre-formed arch forms, or other commercially available materials. In an embodiment, the base unit can be constructed of a thermoplastic material, such as BIOCRYL™ available from Great Lakes Orthodontics of Tonawanda, N.Y., heat molded over a dental model of the patient's teeth. For example, 3 mm BIOCRYL™ can be pressure molded over the dental casts of the lower teeth using a BIOSTAR® thermoplastic molding unit, also available through Great Lakes Orthodontics.

Figure 3:
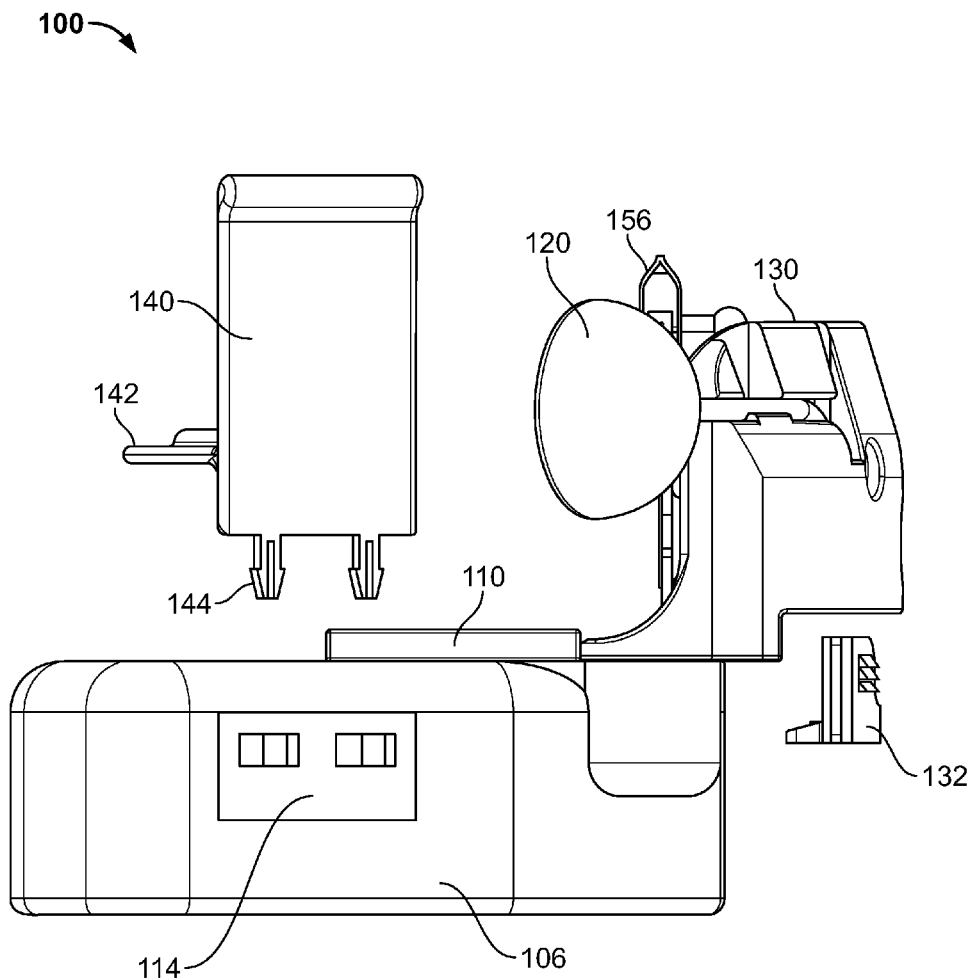
FIG. 3 is a partially exploded side view of the modular device of FIG. 1.

To form the shape shown in FIGS. 1-3, the molded form can be cut in the inner side (i.e. the lingual or tongue side) of the dental arch approximately 3-5 mm below the upper margin of the gum line from the back of the posterior-most tooth on the right completely around the dental arch to the posterior-most tooth on the left. The molded material can then be cut around the outer gingival margin of the molar and bicuspid teeth so that the material forms a right posterior section with a right lateral wall, a right occlusal wall, and right lingual wall, all of which encase the right posterior teeth. The molded material can then be cut in a similar fashion providing a left lateral wall, a left occlusal wall, and a left lingual wall, which provide encasement of the left posterior teeth. The molded material can then be cut to remove the material on the facial or outer surface of the anterior teeth from the right canine tooth to the left canine tooth, leaving an anterior lingual wall which extends from the inside upper edges of the anterior teeth to 3-5 mm below the gum-tooth margin.

Connected with the base unit 102 are one or more modular structures for dilating airways of the patient. The modular structures connectable with the base unit 102 shown in FIG. 1 include a maxillary repositioning flange 130 and a pair of nasio-labial dilators 120 connected with the maxillary repositioning flange 130 for urging the upper lip away from the maxillary dental arch, thereby dilating the nasal passage of the patient. A posterior vestibular pad support 140 is also shown extending from the base unit 102 approximately at the location of the right molar. As will be described in more detail below, the posterior vestibular pad support 140 is connected with a posterior vestibular pad (146 in FIG. 13) which when positioned within the vestibule urges the upper lip surrounding the right side of the maxillary dental arch away from the maxillary dental arch. A brace 142 extending from the posterior vestibular pad support 140 contacts the bite surface 118 of the base unit 102. The brace 142 helps maintain the posterior vestibular pad support 140 in a desired position while relieving stress applied to tines 144 mated with an attachment point 114 extending from the base unit 102. Though not shown, a second posterior vestibular pad support can extend from the left side of the base unit 102, for example in a configuration mirroring that of the right posterior vestibular pad support 140.

Figure 4:
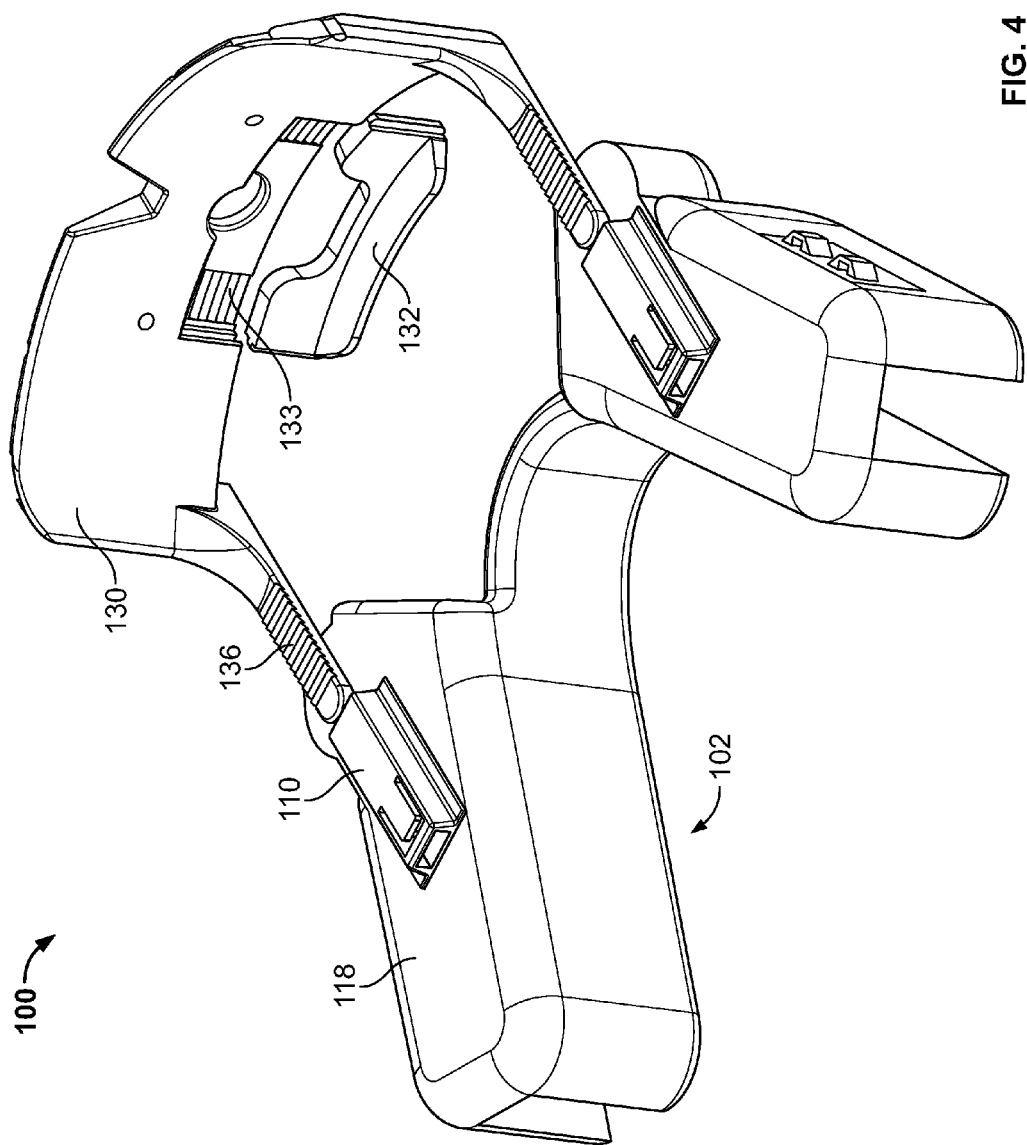
FIG. 4 is a partially exploded posterior view of the modular device of FIG. 1.
Figure 5:
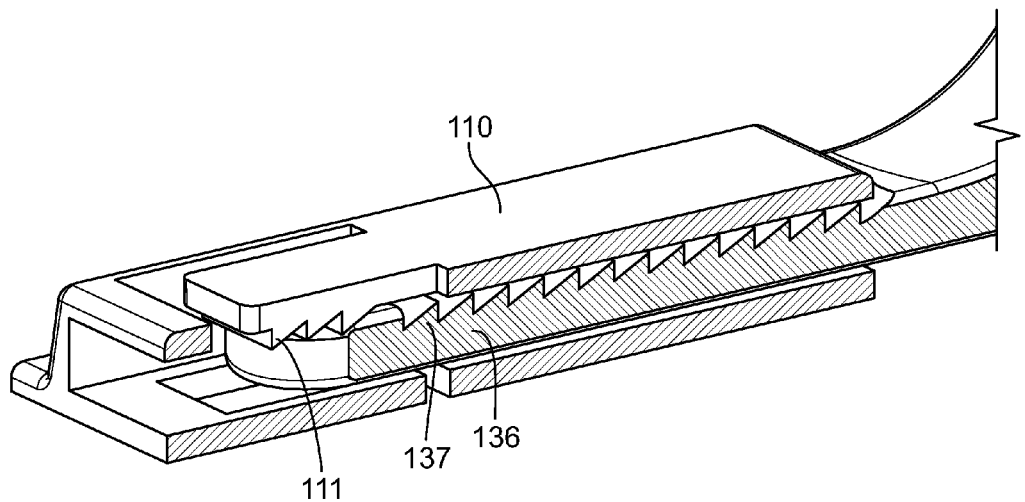
FIG. 5 is a partial cross-section of a ratchet mechanism for adjusting the position of a maxillary repositioning flange relative to a base unit of the modular device of FIG. 1.
Figure 6:
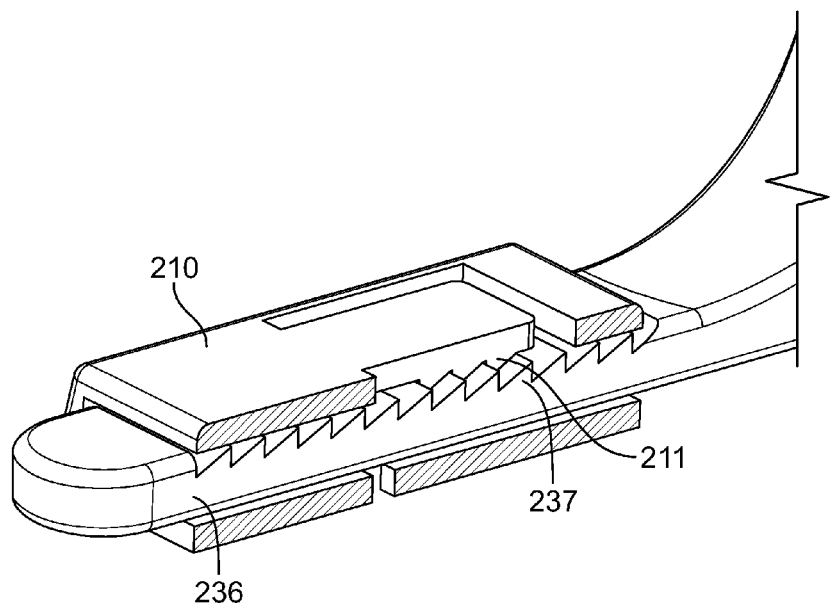
FIG. 6 is a partial cross-section of an alternative ratchet mechanism for adjusting the position of the maxillary repositioning flange relative to the base unit of the modular device of FIG. 1.

FIG. 4 is a partially exploded posterior perspective view of the modular device 100 showing the maxillary repositioning flange 130 separated from the base unit 102 and a support shelf 132 separated from a support shelf pocket 133 within the maxillary repositioning flange 130. The support shelf 132 is adjustably positioned to provide a resting surface for the lower lip of the patient. The maxillary repositioning flange 130 is adjustably connected with the base unit 102 by a ratchet mechanism (more clearly seen in the cross-section of FIG. 5) including a ratchet 136 that is captured within a ratchet housing 110 extending from a bite surface 118 of the base unit 102 by a pawl 111. The ratchet 136 is urged through the ratchet housing until the teeth of the pawl 111 engage the teeth 137 of the ratchet 136. An alternative arrangement is show in FIG. 6, with the pawl 211 reversed within the ratchet housing 210. The ratchet housing 110 can be fixedly connected to the bite surface 118, for example using adhesives or other fastening techniques, or integrally formed with the base unit 102, for example by molding. The base unit 102 and maxillary repositioning flange 130 can be moved relative to each other by advancing the ratchet 136 along the pawl 111 to accommodate different patients and bite patterns, and/or to adjust a patient's prescription. The ratchet 136 can be moved in a direction opposite the ramped surface of the ratchet teeth (i.e., retreated rather than advanced) by lifting the pawl 111 away from the ratchet 136 and moving the ratchet 136 within the ratchet housing 110.

Referring again to FIG. 2, modular structures further include an anterior vestibular pad 156 and a flange spacing pad 158 connected with the maxillary repositioning flange 130. The vestibular pad 156 and flange spacing pad 158 are separate structures that in at least one embodiment are separately expandable and collapsible. When the base unit is seated on the lower jaw, the anterior vestibular pad 156 occupies a space in the vestibule between the upper lip and the maxilla, and urges the upper lip away from the maxilla to thereby dilate the nasal passages. The flange spacing pad 158 is a cushion arranged between the maxillary repositioning flange 130 and the soft tissues of the mouth of the patient. In embodiments where the flange spacing pad 158 volume is adjustable, the flange spacing pad 158 can be expanded or deflated (e.g., by either filling or depleting) to adjust a position of the flange further from or closer to the maxilla, thereby adjusting the relative position of the upper and lower jaws and adjusting the anatomic and functional relationships of the oral pharyngeal structure. In alternative embodiments, the anterior vestibular pad 156 and flange spacing pad 158 can be a single, integrated structure. In other embodiments, the anterior vestibular pad 156 can be separatable from the maxillary repositioning flange 130 independent of the flange spacing pad 158. In still other embodiment, the anterior vestibular pad 156 can eliminated, for example where sufficient upper lip stretching is achieved by way of a pair of nasio-labial dilators 120, or where a treating physician deems repositioning of the lower jaw relative to the upper jaw sufficient to improve airflow without dilating the nasal passages.

Figure 7:
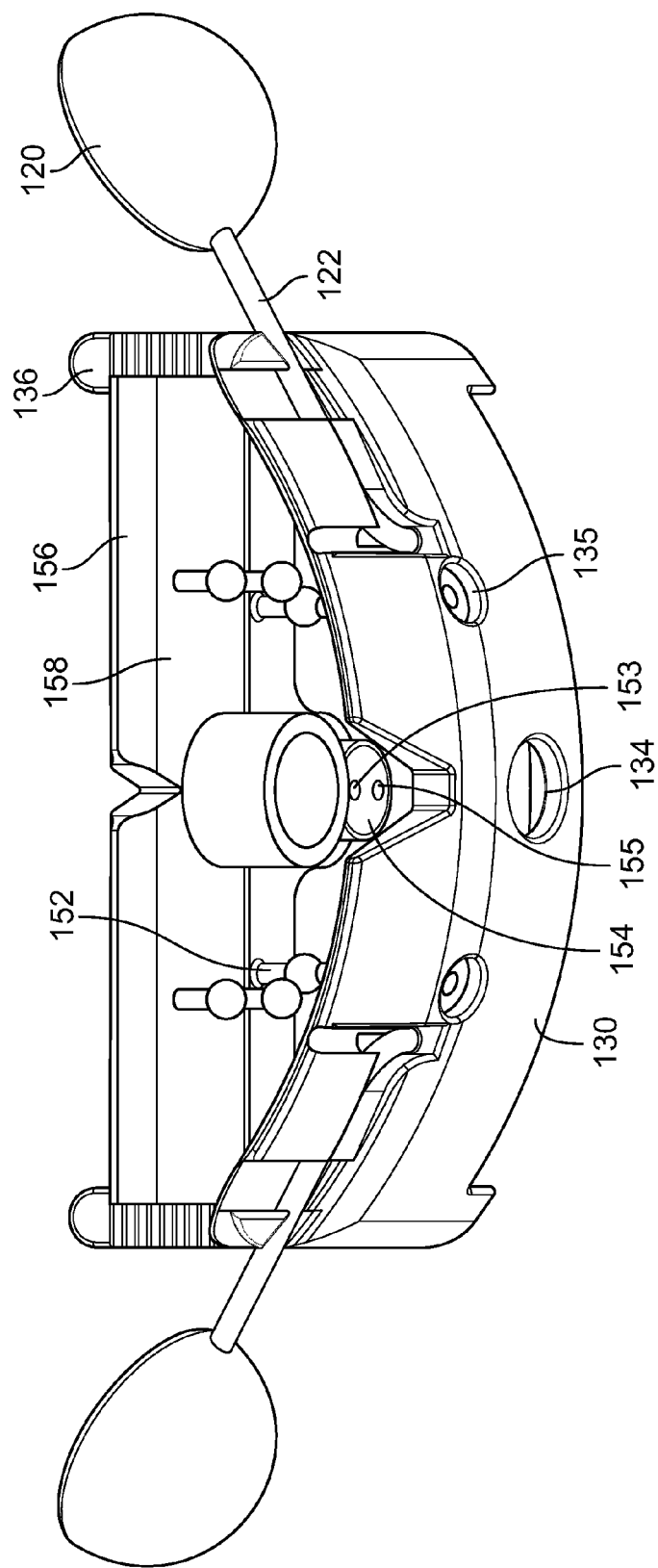
FIG. 7 is a top-down anterior view of the maxillary repositioning flange of FIG. 1.

FIG. 7 is a top-down view of an embodiment of the maxillary repositioning flange 130 isolated from the base unit 102. A pair of pad stems 152 can be seen connecting the flange spacing pad 156 with the maxillary repositioning flange 130 by way of an interference fit with connection points 135 of the maxillary repositioning flange 130. In other embodiments, the anterior vestibular pad 156 and/or the flange spacing pad 158 can be connected with the maxillary repositioning flange 130 using some other structure or technique. In still other embodiments, the anterior vestibular pad 156 and/or the flange spacing pad 158 can be integrally formed with the maxillary repositioning flange, for example by molding. One of ordinary skill in the art, upon reflecting on the present teachings will appreciate the myriad different ways in which the structures of the modular device can be associated with each other.

The anterior vestibular pad 156 and the flange spacing pad 158 can be formed of a pliable material that can be expanded by filling the pliant material with a fluid or collapsed by depleting at least a portion of a fluid within the pliant material. The maxillary repositioning flange 130 includes an access port 134 for accessing an anterior pad valve 154. The anterior pad valve 154 includes an upper injection port 153 for accessing the anterior vestibular pad 156 and a lower injection port 155 for accessing the flange spacing pad 158. The injection ports can be accessed by a syringe or other injection tool for filling or depleting one or both of the anterior vestibular pad 156 and the flange spacing pad 158. When the syringe or other injection tool is withdrawn from an injection port 153, 155, the injection port 153, 155 seals to prevent leakage. In other embodiments, the anterior vestibular pad 156 and the flange spacing pad 156 need not be resizable, and can be cushions of fixed size formed from a single or multiple materials. In such embodiments, a plurality of anterior vestibular pads and/or flange spacing pads mateable with the maxillary repositioning flange and having different sizes and shapes can be made available to a physician for selection based on a patient's anatomy and needs.

Figure 8:
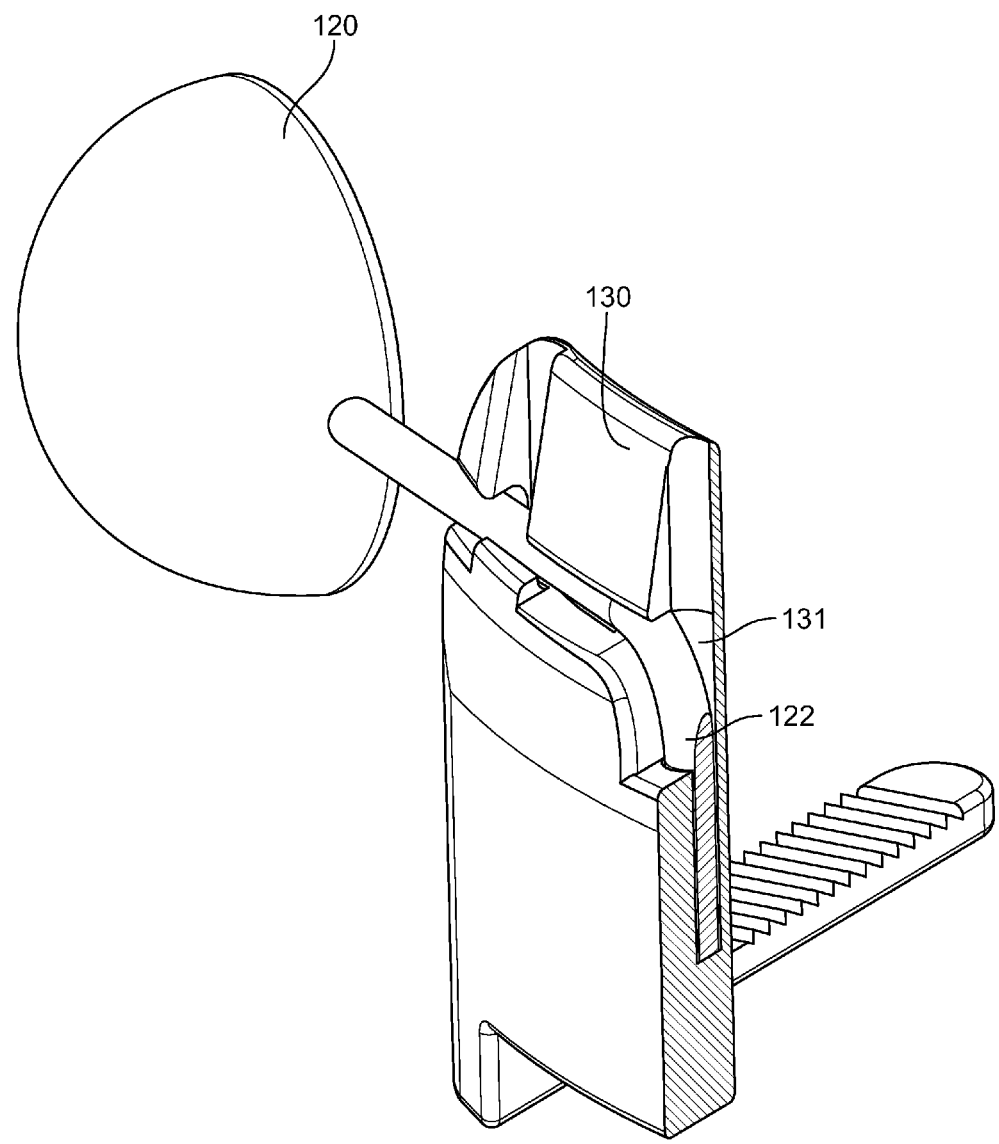
FIG. 8 is a partial cross-section of the maxillary repositioning flange of FIG. 7 illustrating a structure for attaching a nasal dilator to the maxillary repositioning flange.

Referring to FIG. 8, the nasio-labial dilator 120 are connected with the maxillary repositioning flange 130 by a dilator stem 122 extending from the nasio-labial dilator 120. The nasio-labial dilator 120 can be mated with the maxillary repositioning flange 130 by urging the dilator stem 122 into a seated position within a dilator stem pocket 131 of the maxillary repositioning flange 130. The nasio-labial dilator 120 and dilator stem 122 are rotated as necessary until the dilator stem 122 is snapped and held in position within the pocket 131 by tabs passed which the dilator stem 122 is urged during assembly. Applying sufficient pressure can separate the dilator stem 122 from the seated position and allow the nasio-labial dilator 120 and dilator stem 122 to be detached from the maxillary repositioning flange 130 for reconfiguration of the modular device 120. In other embodiments, the dilator stem 122 can be connected to the maxillary repositioning flange 130 using some other structure or technique that allows the dilator stem 122 to be selectively detached from the maxillary repositioning flange 130, such as an attachment point including clasps for capturing and gripping the dilator stem.

As shown in FIGS. 1-8, a nasio-labial dilator has an approximately semi-spherical shape. However, in other embodiments, the nasio-labial dilator can have some other shape. For example, the nasio-labial dilator can be semi-ellipsoidal or disk-like. Further, a nasio-labial dilator can be fixedly connected with a dilator stem, or alternatively, the nasio-labial dilator can be detachable from the dilator stem. The nasio-labial dilator can be formed from a rigid or semi-rigid material, or alternatively the nasio-labial dilator can be formed from a pliable material. In some embodiments, the nasio-labial dilator can comprise a flexible, balloon-like structure fillable with a substance such as a fluid (gas or liquid) or gel to give the nasio-labial dilator shape and strength for urging the upper lip away from the maxilla.

Figure 9:
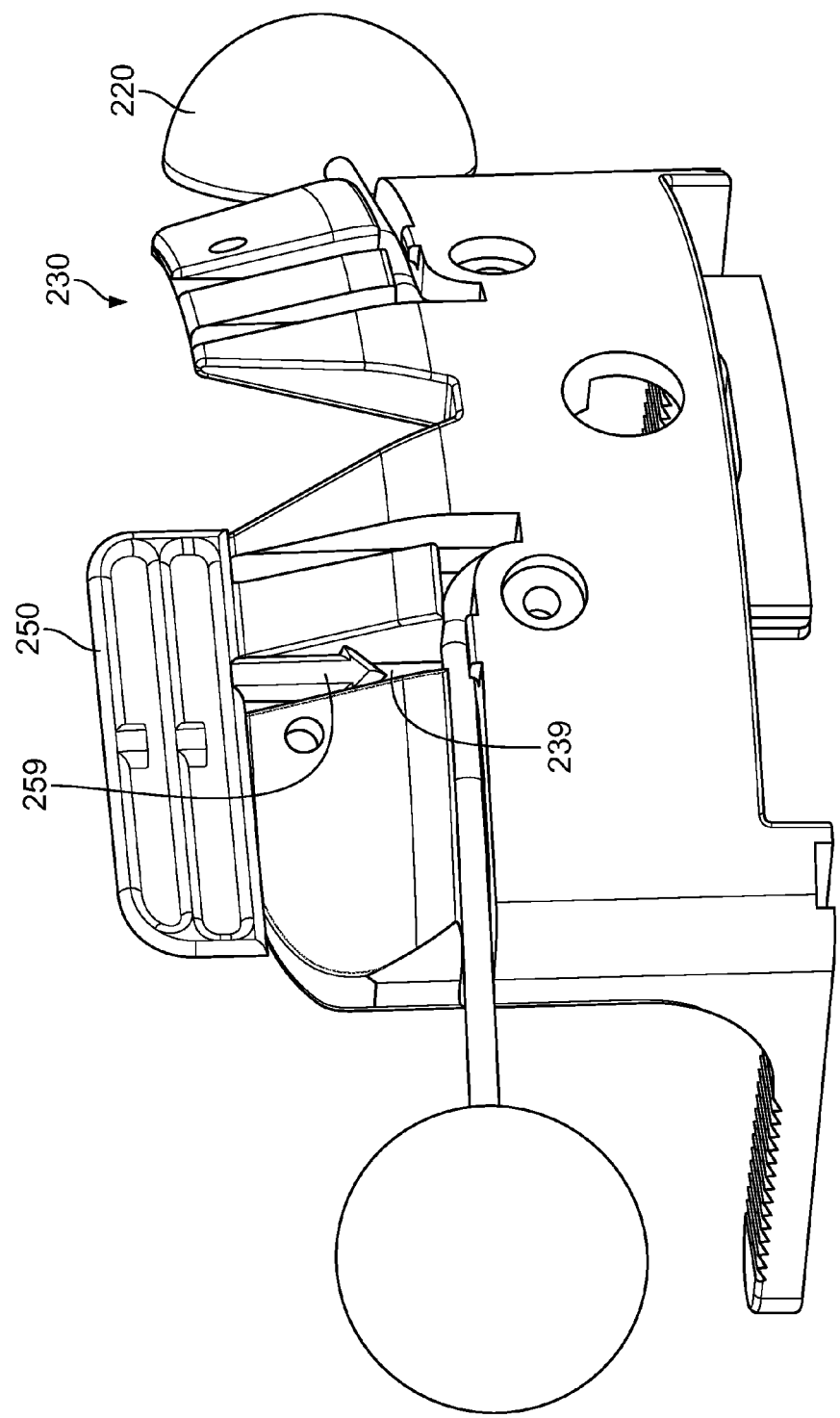
FIG. 9 is a partial detail view of an alternative embodiment of a maxillary repositioning flange usable with a modular device in accordance with the present invention including an anterior vestibular pad support.
Figure 10:
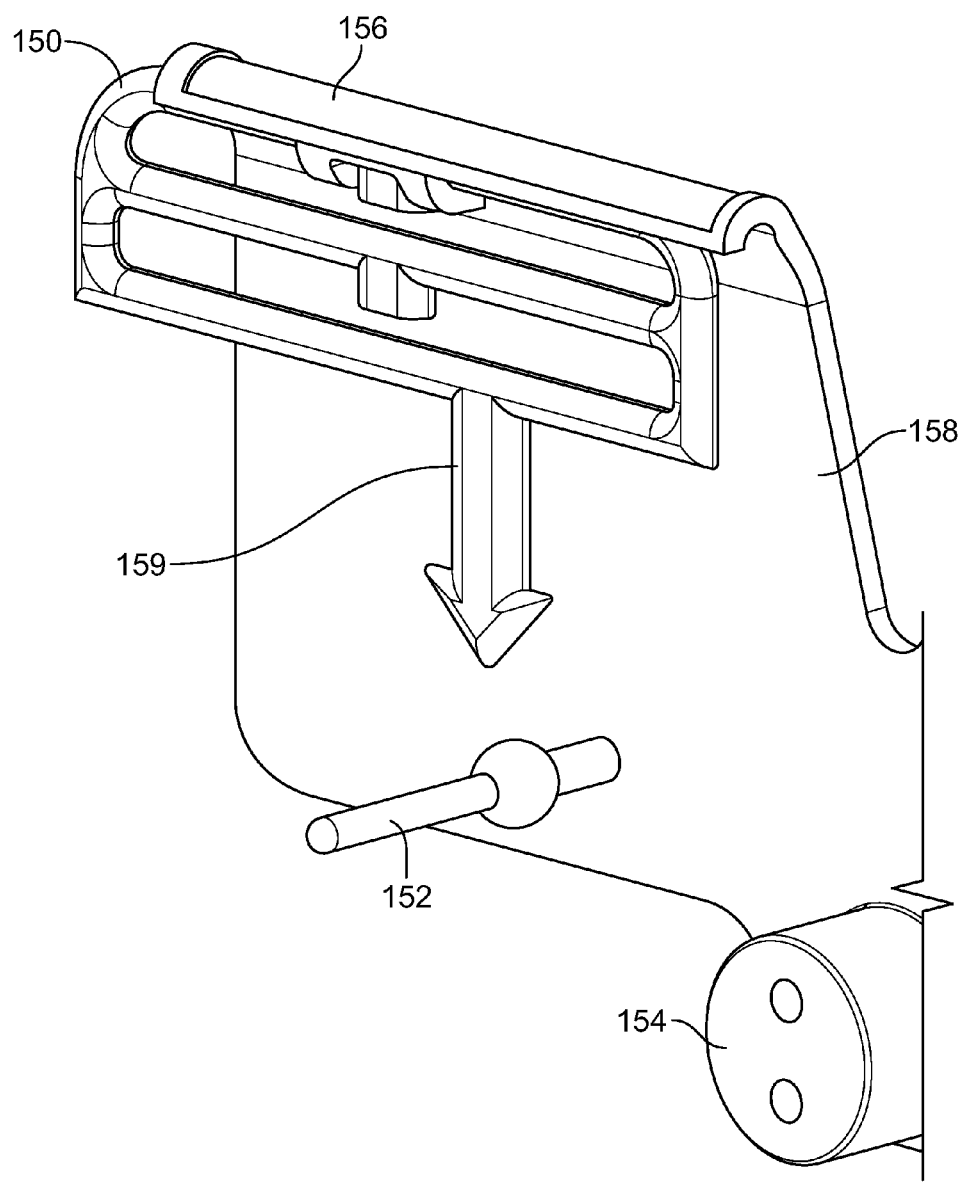
FIG. 10 is a partial detail view of the anterior vestibular pad support of FIG. 9 connected with the anterior vestibular pad and flange spacing pad.

Referring to FIGS. 9 and 10, an alternative embodiment of a maxillary repositioning flange 230 is shown including an anterior vestibular pad support 250 connected with the maxillary repositioning flange 230. As with the nasio-labial dilator 120, the anterior vestibular pad support 250 can be separately mated with the maxillary repositioning flange 230 by urging a support stem 259 into a support stem pocket 239 until the support stem 259 snaps into position. An alternative anterior vestibular pad 256 can partially wrap around and grab the frame of the anterior vestibular pad support 250, which assists in guiding the anterior vestibular pad 256 vertically as the anterior vestibular pad 256 is expanded. The anterior vestibular pad support 250 can provide a point of support to help maintain tension of the anterior vestibular pad 256 and/or the flange spacing pad 258 to resist undesirable collapse or shifts in position of the modular structures.

As can be seen in FIGS. 11-14, the modular structures of the modular device 100 can be selectably attached to the base unit 102 as prescribed by a physician, for example in view of the severity and type of constriction of the airways of the patient and/or the comfort of the patient. Further, the sizes and shapes of the modular structures connected with the base unit 102 can be selected based on the anatomy of the patient and any other factor the patient and/or physician deems relevant.

Figure 11:
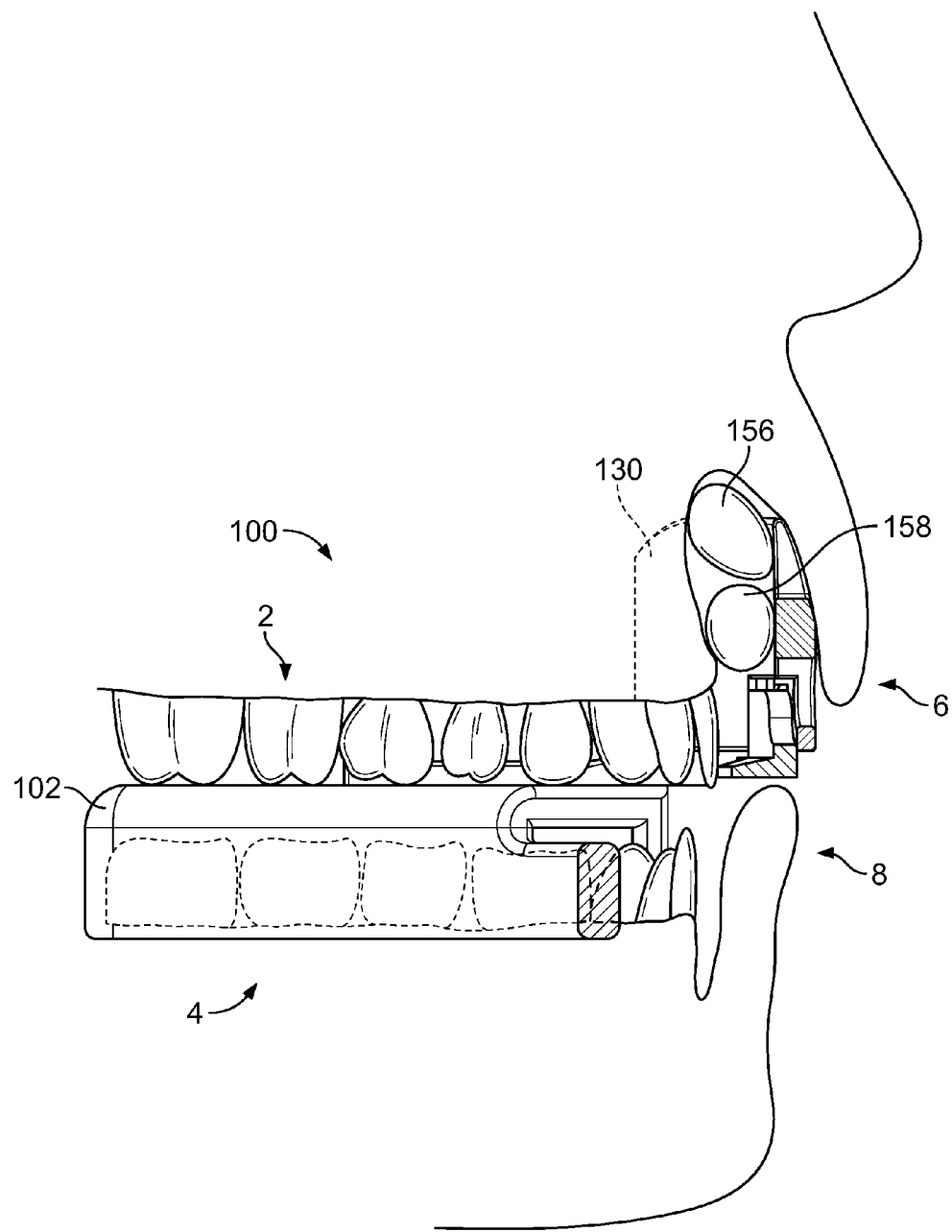
FIG. 11 is a midline cross-section showing a modular device in accordance with the present invention with modular structures including an anterior vestibular pad and a flange spacing pad positioned within the mouth of a patient.

FIG. 11 shows a modular device 100 positioned within the mouth of the patient with the base unit 102 seated on the mandible 4. The modular device 100 comprises a maxillary repositioning flange 130 connected with the base unit 102, an anterior vestibular pad 156 extending from the maxillary repositioning flange 130 into the vestibule between the upper dental arch and the upper lip of the patient, and a flange spacing pad 158 extending from the maxillary repositioning flange 130 to cushion the gums from the maxillary repositioning flange 130. The anterior vestibular pad 156 urges the upper lip 6 away from the maxilla 2, stretching the soft tissue and dilating the air nasal airways. The modular device 100 further urges the mandible 4 forward relative to the maxilla 2. The maxillary repositioning flange 130 and flange spacing pad 158 can correct overbite by requiring the mandible 4 to be positioned forward to accommodate the structures when seating the device in the patient's mouth. Once seated, the maxillary repositioning flange 130 and flange spacing pad 158 obstruct posterior movement of the mandible and tongue. The flange spacing pad 158 distributes the force exerted by the mandible 4 to assume a non-corrected position across the upper dental arch. Holding the mandible 4 in a more forward position using the maxillary repositioning flange 130 can assist in opening airways that may otherwise be blocked by the mandible and tongue while allowing a degree of mobility of the jaw.

The anterior vestibular pad 156 extends upward to fill the vestibule between the maxilla 2 and upper lip 6, thereby stretching the upper lip 6 near the base of the nose. As fluid is added to the anterior vestibular pad 156 by way of the upper injection port 153, the anterior vestibular pad 156 expands upward into the vestibule. Removing fluid from the anterior vestibular pad 156 causes the volume to reduce. The lower lip 8 can contact and rest on the support shelf 132.

The cushioning and separation distance of the maxillary repositioning flange 130 can be controlled by adjusting a volume of a fluid (e.g., air, saline) within the flange spacing pad 158. As fluid is added to the flange spacing pad 158 by way of the lower injection port 155, the flange spacing pad 158 expands pushing the maxilla 2 and maxillary repositioning flange 130 apart. Contrariwise, by removing fluid from the flange spacing pad 158, a gap between the maxilla 2 and maxillary repositioning flange 130 can be reduced. The flange spacing pad 158 provides a mechanism to adjust relative spacing of the maxilla 2 and mandible 4 that supplements the ratchet mechanism connecting the maxillary repositioning flange 130 to the base unit 102. Such a secondary adjustment mechanism can enable adjustment by a technician in a variety of situations where adjusting relative spacing by way of the ratchet mechanism is impractical or inconvenient. For example, a technician can adjust relative spacing of the maxilla 2 and mandible 4 for a sleeping patient during a sleep study without waking the patient. The flange spacing pad 158 can also reduce the need to custom shape the maxillary repositioning flange 130, allowing selection from a finite set of sizes/shapes of flanges with further customization by way of adjusting the volume of the flange spacing pad 158. The flange spacing pad 158 can further eliminate the need for a maxillary dental splint or other device to protect the teeth and the soft tissue associated of the maxilla. The flange spacing pad 158, acting as a cushion, can generally conform with the shape of the maxilla to relieve pressure on the upper teeth.

Figure 12:
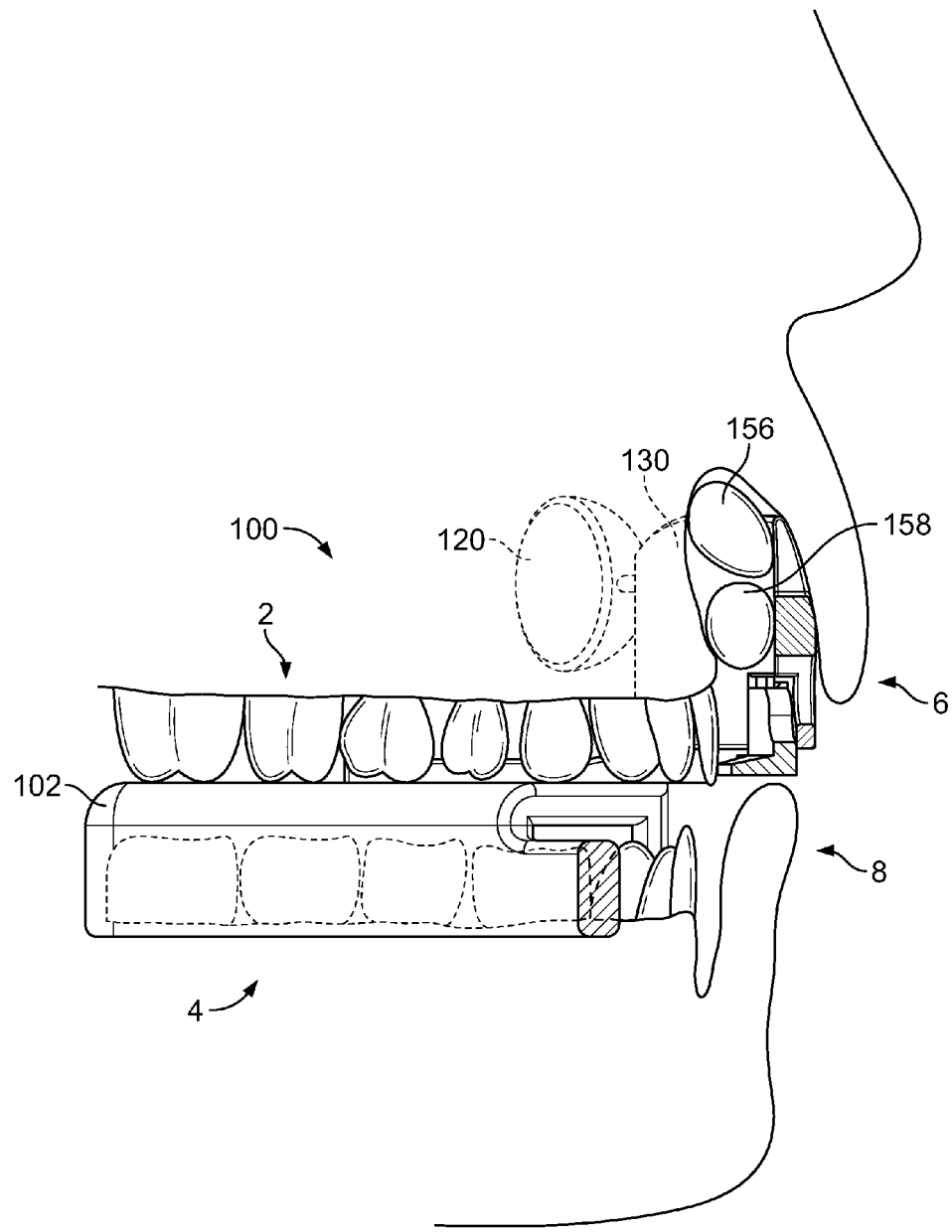
FIG. 12 is a midline cross-section showing a modular device in accordance with the present invention with modular structures including an anterior vestibular pad, a flange spacing pad, a nasal dilator positioned within the mouth of a patient.

FIG. 12 illustrates the modular device 100 of FIG. 11 with an additional modular structure including a nasio-labial dilator 120 connected with the maxillary repositioning flange 130. The nasio-labial dilator 120 stretches the upper lip 6 at a location to the side of the nose, thereby stretching the skin apart to dilate the nasal airways. A nasio-labial dilator 120 is shown extending along the left side of the patient's mouth, acting to stretch the upper lip to the left and away from the patient's maxilla. It should be noted that a second nasio-labial dilator (not shown) also extends along the right side of the patient's mouth acting to stretch the upper lip to the right and away from the patient's maxilla.

Figure 13:
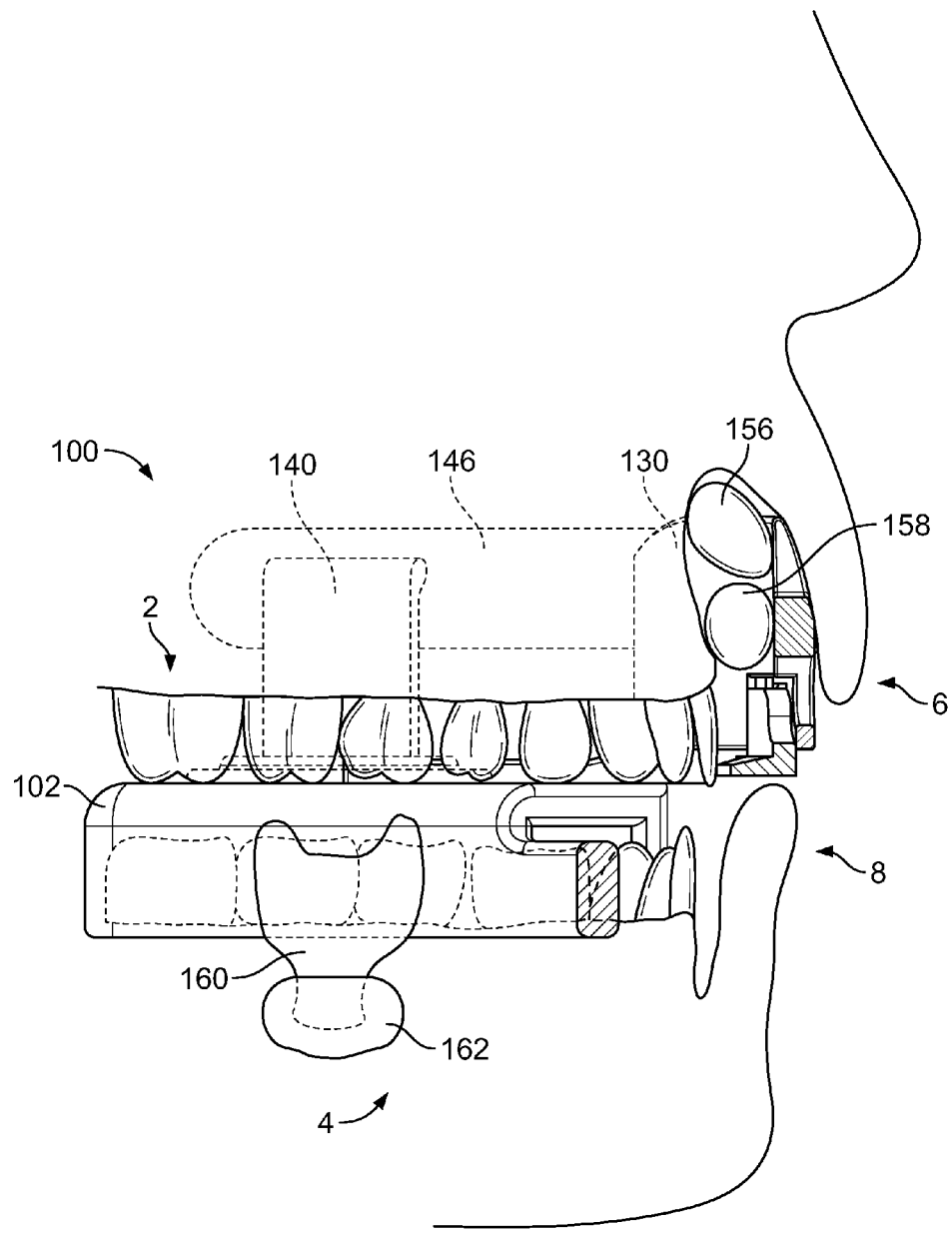
FIG. 13 is a midline cross-section showing a modular device in accordance with the present invention with modular structures including an anterior vestibular pad, a flange spacing pad, a nasal dilator and posterior vestibular pad positioned within the mouth of a patient.
Figure 14:
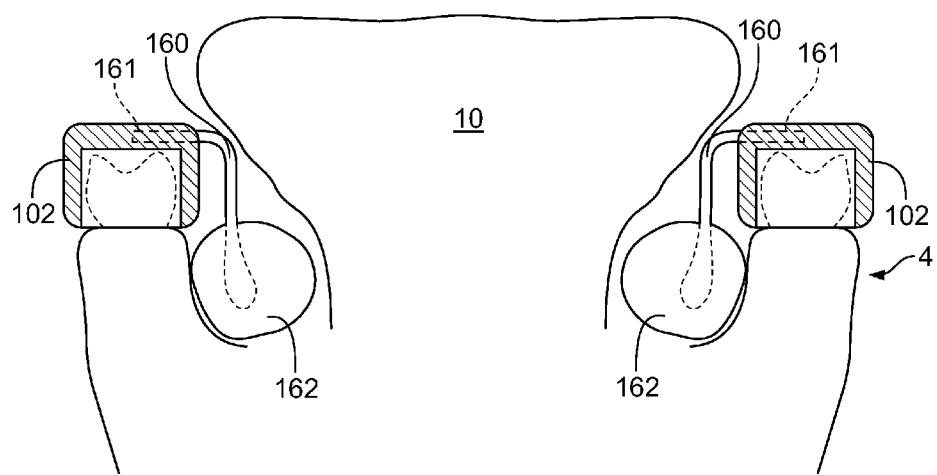
FIG. 14 is a partial cross-section of a modular device in accordance with the present invention seated on the lower jaw of the patient and including tongue positioners arranged under a tongue for urging the tongue again a soft palette of the mouth.

FIGS. 13 and 14 illustrate the modular device 100 of FIG. 11 with additional modular structures including a posterior vestibular pad support 140, a posterior vestibular pad 146, a tongue positioner guide 160 and a tongue positioner. The posterior vestibular pad support 140 is connected with the base unit 102 by way of an attachment point (114 in FIG. 3). The support 140 is connected with a posterior vestibular pad 146 which has a volume that is expandable or collapsible to suitably stretch tissue connected with the maxilla 2 above the dental arch in ranging at least from the canine posterior to the molars. The posterior vestibular pad 146 works in tandem with the anterior vestibular pad 156 to generally stretch tissue associated with the upper lip 6 away from the maxilla 2 along most of the dental arch, range from at least the second molar on the left side to the second molar on the rights side (where a complementary posterior vestibular pad support 140 and balloon 146 are attached on the right side of the base unit 102).

The tongue positioner guides 160 likewise attach to the base unit 102 or are molded into the base unit 102 so that the tongue positioner guides 160 extend from, or are positioned along, the lingual wall 104 of the base unit 102. As shown in FIG. 14, the tongue positioner guides 160 extend under the tongue 10 of the patient and a tongue positioner 162 is connected with the distal end of the support 160 and arranged below the tongue 10. The tongue positioner 162 can have a volume that is expandable or collapsible to suitably elevate the base of the tongue 10, narrowing the lateral width of the tongue 10 and urging the tongue 10 vertically to position the tongue 10 in front of and against the soft palate, which secures the tongue 10 to prevent the tongue 10 from falling back and blocking the pharyngeal airway. In this way, the tongue positioner 162 can assist in opening up the pharyngeal airway (i.e., reducing constriction of the pharynx).

As with the other components described above, such as the nasio-labial dilators, the tongue positioner guide and tongue positioner can be chosen and attached to the modular device depending on the patient's medical needs, the patient's comfort, and the patient's dental anatomy. The modular nature of the device allows a physician to customize the device to individually suit the patient. While the base unit can be shaped using a cast of the patient's dental anatomy, all other components can be selected from pre-made modular structures. Further, the modular structures can be easily attached, removed and replaced, without requiring the creation of a new base unit using a cast. The snap-on/snap-off nature of the device and the expandable/collapsible nature of the balloons make customization a relatively fast and simple process when compared with existing systems, reducing discomfort of the patient and the time demands on the physician. The ratcheting mechanism of the maxillary repositioning flange allows for fast and easy adjustment for changes in prescription, as does the ability to expand or collapse any of the support balloons.

Figure 15:
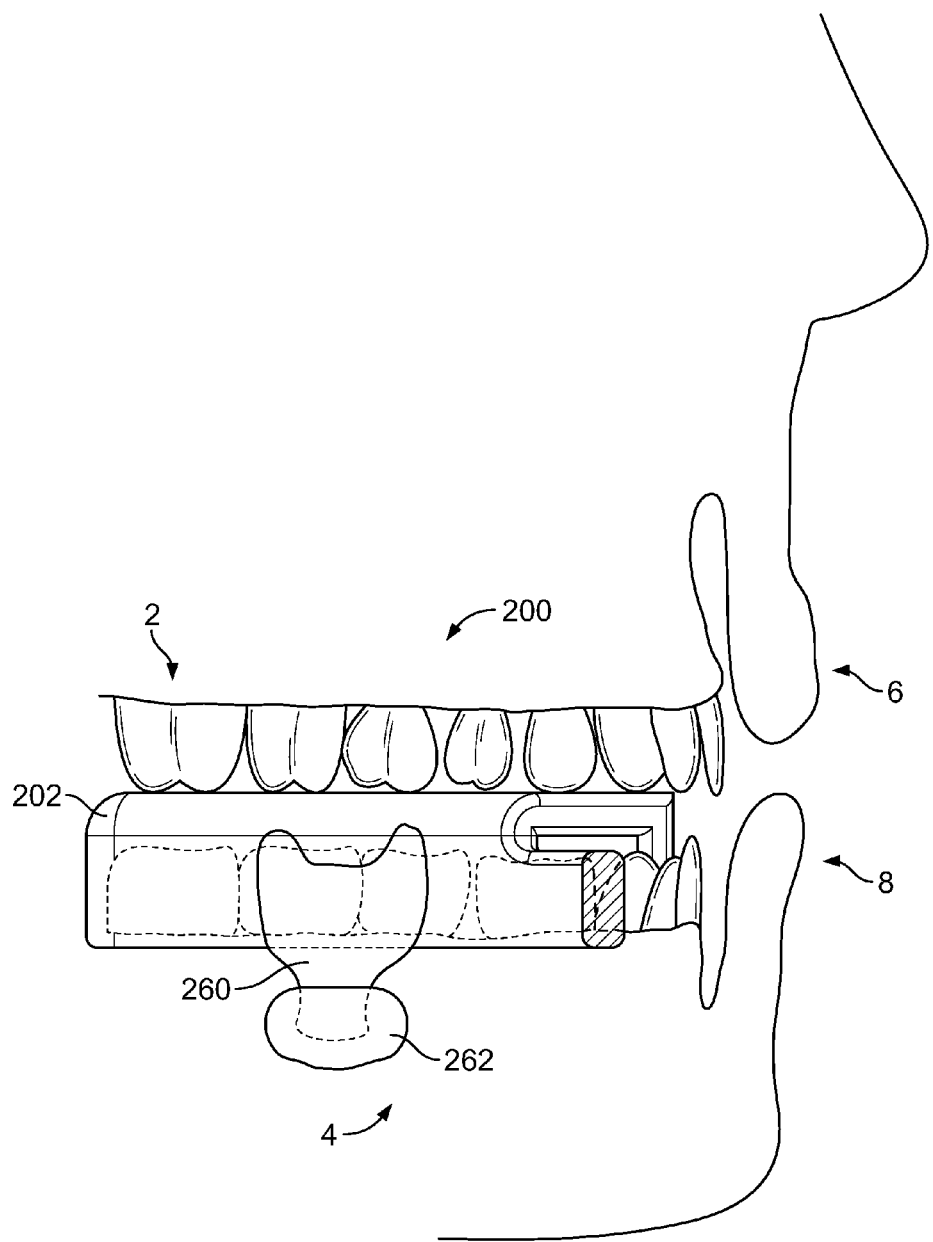
FIG. 15 is a midline cross-section of an alternative modular device in accordance with the present invention seated on the lower jaw of the patient and including tongue positioners arranged under a tongue for urging the tongue again a soft palette of the mouth.

FIG. 15 illustrates an alternative embodiment of a modular device 200 in accordance with the present invention comprising a base unit 202 that is seated on the mandible 4 but does not include a maxillary repositioning flange. The modular device 200 includes a pair of tongue positioner guide 260 and corresponding tongue positioners 262. As above, the tongue positioner guides 260 attach to the base unit 202 or are molded into the base unit 202 so that the tongue positioner guides 260 extend from, or are positioned along, the lingual wall of the base unit 202. As shown, the tongue positioner guides 260 extend under the tongue of the patient and a tongue positioner 262 is connected with the distal end of the support 260 and arranged below the tongue. The tongue positioner 262 can optionally have a volume that is expandable or collapsible to suitably elevate the base of the tongue, narrowing the lateral width of the tongue and urging the tongue vertically to position the tongue in front of and against the soft palate, which secures the tongue to prevent the tongue from falling back and blocking the pharyngeal airway. In this way, the tongue positioner 262 can assist in opening up the pharyngeal airway (i.e., reducing constriction of the pharynx) independent of any additional modular structures.

Figure 16:
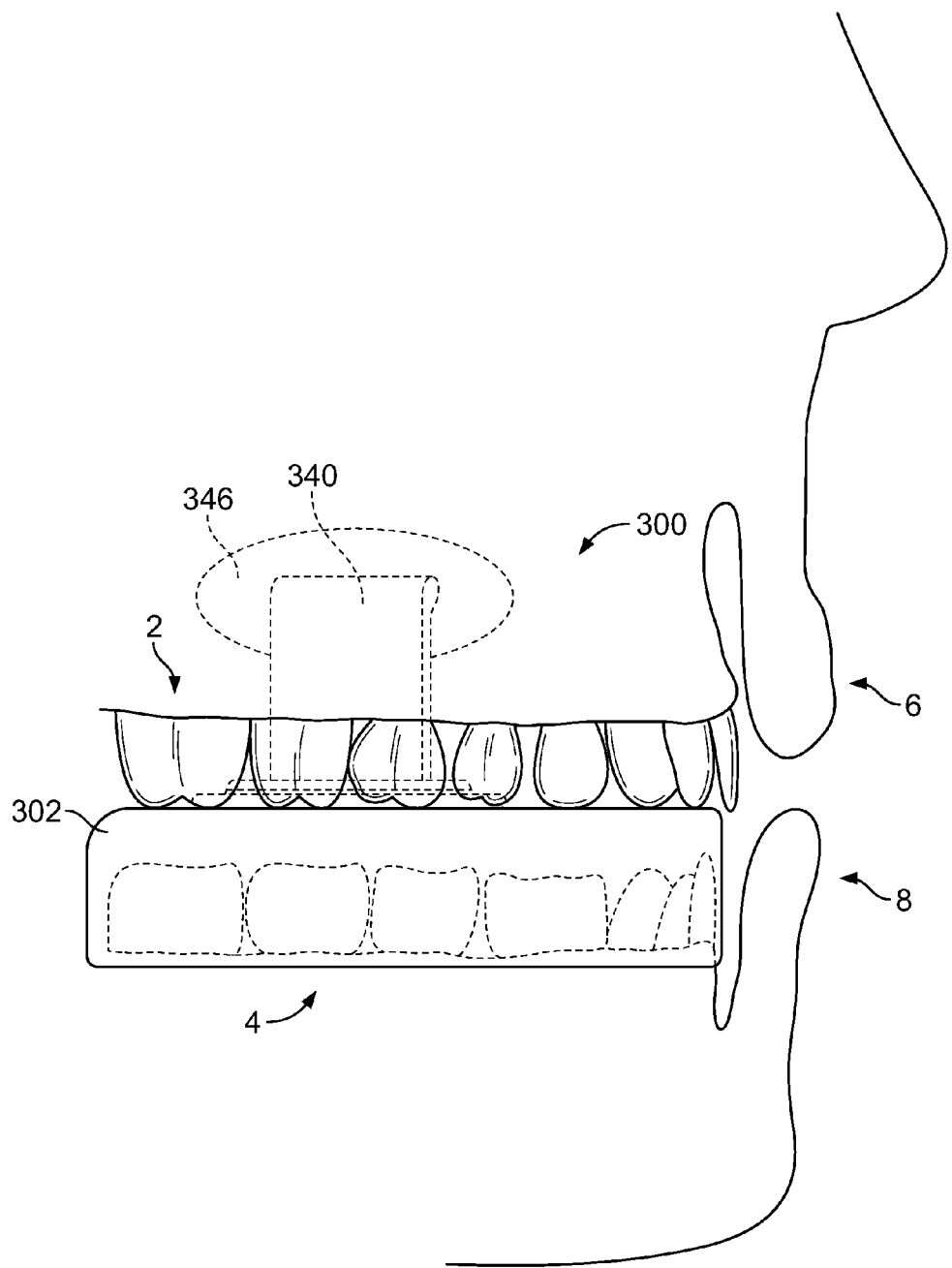
FIG. 16 is a midline cross-section of an alternative embodiment of a modular device in accordance with the present invention seated on the lower jaw of the patient and including a posterior vestibular pad.

FIG. 16 illustrates a further embodiment of a modular device in accordance with the present invention comprising a mouth guard 300 that can be worn during physical activity, for example during participation in sports, to dilate airways and improve air flow. Such a mouth guard can be particularly useful during heavy cardiovascular and aerobic activities when the wearer requires increased levels of oxygen. When a base unit 302 of the mouth guard 300 is seated on the mandible 4, as shown, the mouth guard 300 completely encases the dental arch of the mandible 4 to protect the teeth from physical impact. In other embodiments, some of the teeth may be exposed where protection is not a primary concern (for example the incisors, as shown in FIGS. 1-12). The mouth guard 300 is a modular device and as configured in FIG. 16 includes a posterior vestibular pad support 340 extending from the based unit 302 of the mouth guard 300. A posterior vestibular pad 346 is connected with the support 340 and urges the soft tissues in the vestibule above the molars away from the maxilla 2. The posterior vestibular pad 346 can be resizable, so that the pad 346 can be expanded or collapsed as desired. As above, the size and/or shape of the posterior vestibular support 340 and the volume and/or shape of the posterior vestibular pad 346 can be chosen based on the dental anatomy of the patient, the medical needs of the patient, and/or the level of physical activity the patient plans to engage in.

Figure 17:
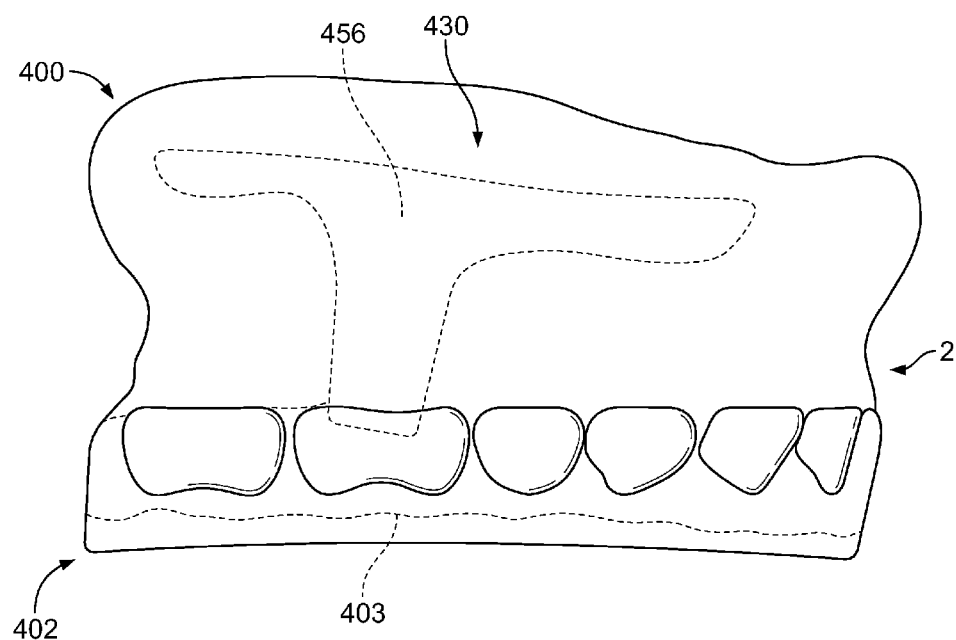
FIG. 17 is an anterior view of a mouth guard in accordance with the present invention seated on the maxillary of the patient including an anterior maxillary flange having a volume adjustable by way of an occlusal chamber.

FIG. 17 illustrates a still further embodiment of a modular device in accordance with the present invention comprising a mouth guard 400 that can be worn during physical activity, for example during participation in sports, to dilate airways and improve air flow. Unlike previously described embodiments, the base unit 402 of the mouth guard 400 is seated on the maxilla 2 and completely encases the dent arch of the maxilla 2 to protect the teeth from physical impact. As above, in other embodiments, some of the teeth may be exposed where protection is not a primary concern (for example the incisors). The mouth guard 400 includes a maxillary flange 430 extending from the base unit 402 that occupies the vestibule between the upper lip and the upper dental arch. An anterior vestibular pad 456 can forms an expandable and collapsible space within the maxillary flange 430. An occlusal chamber 403 is connected with the anterior vestibular pad 456 so that a fluid and/or gel can be exchanged between the spaces. Distribution of fluid and/or gel is balanced between the occlusal chamber 403 and anterior vestibular pad 456 by elastic resistance of the maxillary flange 430. As the wearer bites down on the mouth guard 400 so that the teeth are clenched, pressure is applied to the occlusal chamber 403 by the jaw, collapsing the occlusal chamber 403 and urging the fluid and/or gel occupying the occlusal chamber 403 upward into the anterior vestibular pad 456. The anterior vestibular pad 456 expands as the fluid and/or gel fills the anterior vestibular pad 456 due to the forced evacuation of the occlusal chamber 403, causing the maxillary flange 430 to expand and further dilate the nasal airways by expanding the vestibule and stretching the skin around the nasal airways. Expansion mechanics of the maxillary flange 430 can result naturally from need, as an increase in intensity of a wearer and/or physical stress will generally result in a wearer clenching his/her jaw in response. A heightened stress condition is one that can benefit from an increase in oxygen and heavier breathing, making expansion of the vestibular space and resulting dilation of the nasal airway a beneficial response to clenching of the jaw.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

The invention claimed is:

1. A device adapted to be positioned at least partially in a mouth of a user to reduce resistance of air flow in the oral pharyngeal region and to improve anatomic and functional relationships of the oral pharyngeal structure, the device comprising:
 a base unit adapted to be removably mounted on a lower jaw of the mouth;
 a pair of tongue positioner guides, each tongue positioner guide connected at a proximal end to the base unit; and
 a pair of tongue positioners, each tongue positioner connected with a distal end of a corresponding tongue positioner guide; and wherein each tongue positioner guide comprises a bendable material so that the tongue positioners are repositionable relative to the base unit;

wherein when the base unit is mounted on the lower jaw, the tongue positioners are adapted to be arranged beneath a tongue of the mouth so that the tongue is urged against a soft palette of the mouth to thereby reduce resistance of air flow in the oral pharyngeal region and improve anatomic and functional relationships of the oral pharyngeal structure.

2. The device of claim 1, wherein the base unit includes an occlusal wall, a lateral wall, and a lingual wall;

wherein the occlusal wall, the lateral wall and the lingual wall provide a structure for receiving at least a portion of the lower jaw.

3. The device of claim 2, wherein the pair of tongue positioner guides extend from the lingual wall of the base unit on opposite sides of the base unit.

4. The device of claim 1, wherein each of the tongue positioner guides is removably connected to the base unit by a fastener.

5. The device of claim 4, wherein the fastener is a snap or a clasp.

6. The device of claim 1, wherein each of the tongue positioners is selectively resizable by adding or removing a fluid from the tongue positioner; and wherein resizing the tongue positioner adjusts an elevation and lateral width of the tongue within the mouth.

7. The device of claim 1, wherein the base unit is molded to the proximal end of the tongue positioner guides.

8. A device adapted to be positioned at least partially in a mouth of a user to reduce resistance of air flow in the oral pharyngeal region and to improve anatomic and functional relationships of the oral pharyngeal structure, the device comprising:

a base unit adapted to be removably mounted on a lower jaw of the mouth;

a pair of tongue positioner guides, each tongue positioner guide connected at a proximal end to the base unit; and a pair of tongue positioners, each connected with a distal end of a corresponding tongue positioner guide; and wherein when the base unit is mounted on the lower jaw, the tongue positioners are adapted to be arranged beneath a tongue of the mouth so that the tongue is urged against a soft palette of the mouth to thereby reduce resistance of air flow in the oral pharyngeal region and improve anatomic and functional relationships of the oral pharyngeal structure;

wherein each of the tongue positioners is selectively resizable by adding or removing a fluid from the tongue positioner; and wherein resizing the tongue positioner adjusts an elevation and lateral width of the tongue within the mouth.

9. The device of claim 8, wherein the base unit includes an occlusal wall, a lateral wall, and a lingual wall;

wherein the occlusal wall, the lateral wall and the lingual wall provide a structure for receiving at least a portion of the lower jaw.

10. The device of claim 9, wherein the pair of tongue positioner guides extend from the lingual wall of the base unit on opposite sides of the base unit.

11. The device of claim 8, wherein each of the tongue positioner guides is removably connected to the base unit by a fastener.

12. The device of claim 11, wherein the fastener is a snap or a clasp.

13. The device of claim 8, wherein each of the tongue positioner guides comprises a bendable material so that the pair of tongue positioners are repositionable relative to the base unit.

14. The device of claim 8, wherein the base unit is molded to the proximal end of the tongue positioner guides.

15. A device adapted to be positioned at least partially in a mouth of a user to reduce resistance of air flow in the oral pharyngeal region and to improve anatomic and functional relationships of the oral pharyngeal structure, the device comprising:

a base unit adapted to be removably mounted on a lower jaw of the mouth;

a pair of tongue positioner guides, each tongue positioner guide connected at a proximal end to the base unit; and a pair of tongue positioners, each connected with a distal end of a corresponding tongue positioner guide; and wherein each of the tongue positioner guides comprises a bendable material so that the pair of tongue positioners are repositionable relative to the base unit;

wherein when the base unit is mounted on the lower jaw, the tongue positioners are adapted to be arranged beneath a tongue of the mouth so that the tongue is urged against a soft palette of the mouth to thereby reduce resistance of air flow in the oral pharyngeal region and improve anatomic and functional relationships of the oral pharyngeal structure;

wherein each of the tongue positioners is selectively resizable by adding or removing a fluid from the tongue positioner; and wherein resizing the tongue positioner adjusts an elevation and lateral width of the tongue within the mouth.

16. The device of claim 15, wherein the base unit includes an occlusal wall, a lateral wall, and a lingual wall;

wherein the occlusal wall, the lateral wall and the lingual wall provide a structure for receiving at least a portion of the lower jaw.

17. The device of claim 16, wherein the pair of tongue positioner guides extend from the lingual wall of the base unit on opposite sides of the base unit.

18. The device of claim 15, wherein each of the tongue positioner guides is removably connected to the base unit by a fastener.

19. The device of claim 18, wherein the fastener is a snap or a clasp.

20. The device of claim 15, wherein the base unit is molded to the proximal end of the tongue positioner guides.

* * * * *